US006223947B1

(12) United States Patent
Bernard

(10) Patent No.: US 6,223,947 B1
(45) Date of Patent: May 1, 2001

(54) EYE DROPPER WITH ILLUMINATED TIP

(75) Inventor: Byron W. Bernard, 1551 Dixie Hwy., Covington, KY (US) 41011

(73) Assignee: Byron W. Bernard, Covington, KY (US)

( * ) Notice: Subject to any disclaimer, the term of this patent is extended or adjusted under 35 U.S.C. 154(b) by 0 days.

(21) Appl. No.: 09/495,394

(22) Filed: Jan. 31, 2000

Related U.S. Application Data
(60) Provisional application No. 60/118,297, filed on Feb. 2, 1999.

(51) Int. Cl.[7] ................................................. B65D 47/18
(52) U.S. Cl. ........................ 222/113; 222/420; 222/156; 604/295
(58) Field of Search ..................... 222/420, 113, 222/156; 604/295, 294, 291, 289

(56) References Cited

U.S. PATENT DOCUMENTS

| | | | |
|---|---|---|---|
| 72,108 | 12/1867 | Stephens | 604/294 |
| 2,382,771 | 8/1945 | Bowers | 604/300 |
| 2,547,450 * | 4/1951 | Du Pont | 222/0 |
| 2,736,316 | 2/1956 | Stovall | 604/300 |
| 3,779,245 | 12/1973 | Windsor | 128/233 |
| 3,845,764 | 11/1974 | Windsor | 128/233 |
| 3,913,575 | 10/1975 | Windsor | 128/233 |
| 4,344,430 | 8/1982 | Astrove | 128/233 |
| 4,515,295 | 5/1985 | Dougherty | 222/113 |
| 4,550,866 | 11/1985 | Moore | 222/420 |
| 4,629,456 | 12/1986 | Edwards | 604/300 |
| 5,133,702 * | 7/1992 | Py | 604/302 |
| 5,342,327 * | 8/1994 | Epstein | 604/294 |
| 5,373,964 | 12/1994 | Moore | 222/1 |
| 5,387,202 * | 2/1995 | Baron | 604/300 |
| 5,558,653 | 9/1996 | Lindstrom | 604/295 |
| 5,584,823 | 12/1996 | Valberg | 604/294 |
| 5,607,410 | 3/1997 | Branch | 604/302 |

FOREIGN PATENT DOCUMENTS 2 053 840  2/1981  (GB) .

\* cited by examiner

*Primary Examiner*—Kenneth Bomberg
*Assistant Examiner*—Stephanie L. Willatt
(74) *Attorney, Agent, or Firm*—Wood, Herron & Evans, LLP

(57) ABSTRACT

An eye dropper bottle for application of opthalmic solutions to the eye includes a bottom wall which is a convex lens which collects light and is configured to focus the ambient light at about the tip of the eye dropper. Thus when an individual utilizes this device, the bottom wall of the eye dropper is focused at a light source such as an incandescent light and as the individual applies the solution to his eyes. The light from the light source will pass through the lens, collect at the tip illuminating the tip relative to the surrounding dropper bottle.

6 Claims, 1 Drawing Sheet

EYE DROPPER WITH ILLUMINATED TIP

This application claims the benefit of U.S. Provisional Application No. 60/118,297, filed Feb. 2, 1999.

BACKGROUND

The proper application of opthalmic solutions using an eye dropper or dropper bottle is problematic for many individuals. It is difficult for an individual to properly align the tip of the dropper with their eye. This problem is frequently compounded by poor vision.

There have been many attempts to resolve this issue. It has been suggested to provide a target ring for an eye dropper in U.S. Pat. No. 4,629,456. Other references have suggested illuminating the eye dropper tip using for example a flashlight as disclosed in U.S. Pat. No. 5,584,823. Merely changing the color or providing a target for the tip of an eye dropper is relatively ineffectual. Using a flashlight to illuminate the tip of an eye dropper is cumbersome and expensive. Others have incorporated illuminating devices into the eye droppers themselves such as disclosed in U.S. Pat. No. 5,558,653 but these are expensive and increase the size of the dropper bottle.

SUMMARY OF THE INVENTION

Accordingly it is the object of the present invention to provide an eye dropper with an illuminated tip. Further, it is an object of the present invention to provide one without a separate attached light source. These objects are achieved by incorporating a light collecting or convex lens in the base or bottom wall of the eye dropper. When the eye dropper is raised toward the eye, the bottom side is pointed towards a light source either natural or man-made such as a window or overhead light. Light will pass through the lens and be focused on the tip of the eye dropper illuminating the tip. This provides an effective, inexpensive method to facilitate application of opthalmic solutions.

This invention will be further appreciated in light of the following detail and description and drawings in which:

DETAILED DESCRIPTION

Figure 1:
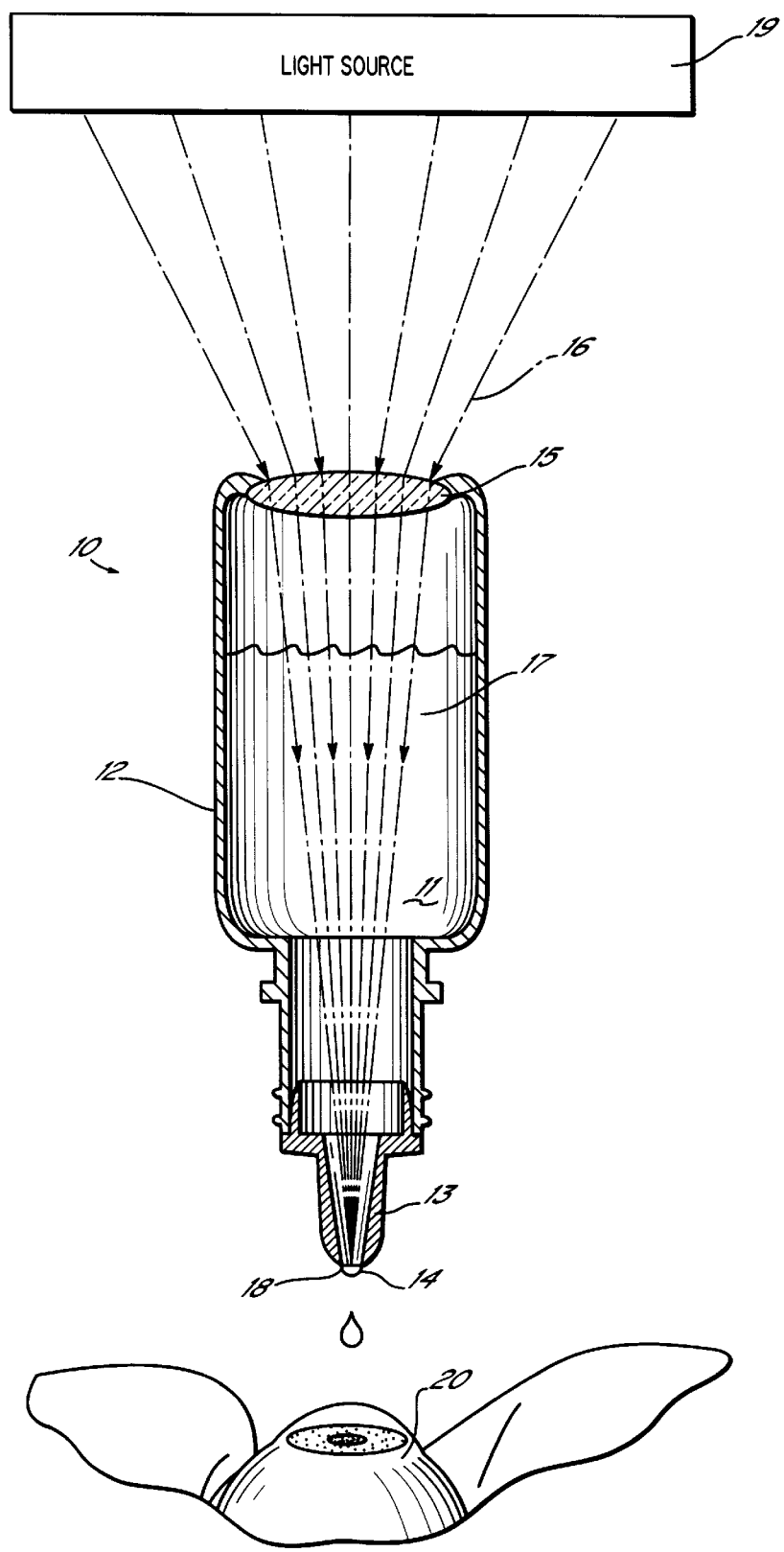
FIG. 1 is a dropper bottle shown in cross-section as it is used in the present invention.

As shown in the FIGURE, the present invention is a squeeze bottle 10 to dispense drops of opthalmic drugs or solutions or other liquids into the eye. Container 10 as shown is partially filled with a transparent or translucent liquid 11. The container has a side wall 12 and tip 13 with an opening 18 which as shown has a drop 14 of the liquid forming. Generally the side wall 12 is formed from an opaque plastic although it can be transparent and the tip is formed from a translucent material. However this can be transparent or opaque.

The container further includes a bottom which is in the form of a light collecting transparent lens. The lens as shown is a convex lens configured to focus ambient light passing through the lens onto the tip portion 13 of the dispenser so as to illuminate a drop 14 as it is dispensed. As shown, the light is focused directly on the opening 18 in 13. Due to the effect of the liquid 11 on the light, the focal point may move around the tip 13. But it will still illuminate the drop 14 as long as it is focused near the tip 13.

The container 10 of the present invention can be formed using common injection molding techniques. The lens or bottom 15 can be coextruded with the side walls or can be a preform and is preferably a clear transparent plastic. However it can be colored plastic which in turn would cause the light shining on the drop 14 to be illuminated with a selected color. The size of the lens 15 can be designed as desired to incorporate more light. The larger the lens, the more light that will be collected and focused at the tip portion 13. This will in turn affect the diameter of the bottle.

As shown in the figure, the user directs the lens 15 toward a light source 19 and the tip above the eye 20. Light rays 16 pass through lens 15 which causes the light rays 17 in the bottle to focus at tip 13 and drop 14. When one is using the eye dropper and looks upwardly at the drop, the tip of the dropper will be illuminated which facilitates aligning the dropper relative to the eye to ensure that the drop falls into the eye.

This container 10 can be used with any solution which will permit light to pass therethrough. The present invention facilitates correct application of drops to an individual's eye without any significant increase in the cost of the dropper bottle. Further it does not require any apparatus that makes the dropper bottle awkward to use nor does it require any batteries or separate light sources.

This has been a description of the present invention along with the preferred method of practicing the invention.

However, the invention itself should only be defined by the appended claims wherein we claim:

1. A dropper bottle having a dispensing tip having an opening and a bottom wall, said bottom wall comprising a transparent lens adapted to focus light passing through said lens on said tip whereby drops of fluid from said dropper bottle are illuminated as they are dispensed.

2. The dropper bottle claimed in claim 1 wherein said dropper bottle includes a side wall and said side wall is an opaque material.

3. The dropper bottle claimed in claim 1 wherein said dispensing tip is translucent.

4. The dispenser claimed in claim 1 containing an opthalmic solution.

5. The dropper bottle claimed in claim 4 wherein said opthalmic solution is transparent.

6. The dropper bottle claimed in claim 4 wherein said opthalmic solution is translucent.

\* \* \* \* \*